(12) United States Patent
Gobbi et al.

(10) Patent No.: US 7,825,123 B2
(45) Date of Patent: Nov. 2, 2010

(54) ISOXAZOLO[4,5]PYRIDIN-3-YL-PIPERAZIN DERIVATIVES USEFUL AS MODULATORS OF DOPAMINE D3 RECEPTORS

(75) Inventors: Luca Gobbi, Muttenz (CH); Georg Jaeschke, Basel (CH); Rosa Maria Rodriguez Sarmiento, Basel (CH); Lucinda Steward, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/561,497

(22) Filed: Sep. 17, 2009

(65) Prior Publication Data
US 2010/0075981 A1    Mar. 25, 2010

(30) Foreign Application Priority Data
Sep. 23, 2008    (EP)    ................................. 08164904

(51) Int. Cl.
*A61K 31/424*    (2006.01)
*C07D 498/04*    (2006.01)

(52) U.S. Cl. ................................. 514/253.04; 544/362
(58) Field of Classification Search ........................ None
See application file for complete search history.

(56) References Cited

FOREIGN PATENT DOCUMENTS

WO    WO 2007/148208    12/2007
WO    WO 2009/013212    1/2009

OTHER PUBLICATIONS

Missale et al., Physiol. Rev. vol. 78 pp. 189-225 (1998).
Gurevich E. V., Neuropsychopharmacology vol. 20 pp. 60-80 (1999).
Joyce J. N., Drug Discovery Today 1, vol. 10, No. 13 pp. 917-925 (2005).
Gurevich E.V., Arch. Gen. Psychiatry vol. 54 pp. 225-232 (1997).
Knutsen et al. Biorg. Med. Chem. Lett. vol. 17 (2007) pp. 662-667.

*Primary Examiner*—Emily Bernhardt
(74) *Attorney, Agent, or Firm*—George W. Johnston; Patricia S. Rocha-Tramaloni; Kimberly J. Prior

(57) ABSTRACT

The present invention provides compounds of formula I, having affinity and selectivity for the dopamine D3 receptors, their manufacture, pharmaceutical compositions containing them and their use for the therapeutic and/or prophylactic treatment of cognitive disorders.

(I)

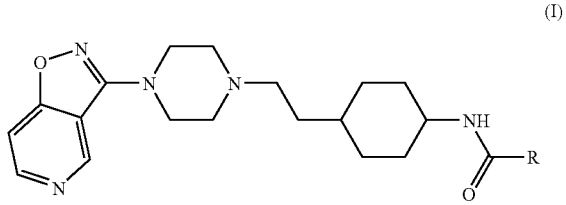

21 Claims, No Drawings

ISOXAZOLO[4,5]PYRIDIN-3-YL-PIPERAZIN DERIVATIVES USEFUL AS MODULATORS OF DOPAMINE D3 RECEPTORS

PRIORITY TO RELATED APPLICATION(S)

This application claims the benefit of European Patent Application No. 08164904.8, filed Sep. 23, 2008, which is hereby incorporated by reference in its entirety.

BACKGROUND INFORMATION

Dopamine, a major catecholamine neurotransmitter, is involved in the regulation of a variety of functions which include emotion, cognition, motor functions, and positive reinforcement, (Purves, D. et al. (2004) Neuroscience. Sinauer, third edition, Sunderland, Mass.). The biological activities of dopamine are mediated through G protein-coupled receptors (GPCRs) and in human, five different dopamine receptors $D_1$-$D_5$ have been identified, where the $D_2$-like receptors ($D_2$, $D_3$ and $D_4$) couple to the G-protein $G_{\alpha 1}$ (Missale, C. et al. (1998) Dopamine receptors: from structure to function. Physiol. Rev. 78, 189-225). The $D_3$ dopamine receptor is most highly expressed in the nucleus accumbens (Gurevich, E. V., Joyce, J. N. (1999).

Distribution of dopamine D3 receptor expressing neurons in the human forebrain: comparison with D2 receptor expressing neurons. Neuropsychopharmacology 20, 60-80), and is proposed to modulate the mesolimbic pathway consisting of neuronal projections from the ventral tegmental area, hippocampus and amygdala to the nucleus accumbens, which projects to the prefrontal and cingulate cortices as well as various thalamic nuclei.

The limbic circuit is thought to be important for emotional behavior and thus $D_3$ receptor antagonists are proposed to modulate psychotic symptoms such as hallucinations, delusions and thought disorder (Joyce, J. N. and Millan, M. J., (2005) Dopamine D3 receptor antagonists as therapeutic agents. Drug Discovery Today, 1 July, Vol. 10, No. 13, 917-25), while these antagonists spare the $D_2$ modulated striatal extrapyramidal system (associated with EPS induction). In addition, it has been reported that drug naive schizophrenic patients show altered levels of $D_3$ receptor expression (Gurevich, E. V. et al. (1997) Mesolimbic dopamine D3 receptors and use of antipsychotics in patients with schizophrenia. A postmortem study. Arch. Gen. Psychiatry 54, 225-232) and dopamine release (Laruelle, M. (2000) Imaging dopamine dysregulation in schizophrenia: implication for treatment. Presented at Workshop Schizophr.: Pathol. Bases and Mech. Antipsychotic Action, Chicago), indicating that a disturbed homeostasis of dopamine plays an important role in the etiology of schizophrenic symptoms.

SUMMARY OF THE INVENTION

The present invention provides compounds of formula I, (I)

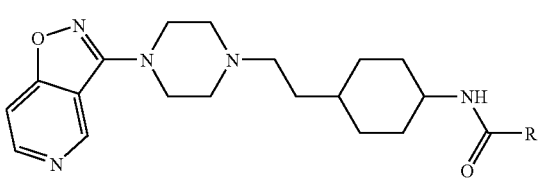

wherein:

R is $C_{1-6}$-alkyl;
  $C_{1-6}$-alkyl substituted by one 3 to 6 membered monocyclic cycloalkyl, $C_{1-6}$-alkoxy, or 1 to 3 halogen atoms;
  $C_{1-6}$-alkoxy;
  aryl;
  aryl substituted by 1 to 3 halogen atoms;
  heteroaryl; or
  heteroaryl substituted by 1 to 3 halogen atoms;

as well as pharmaceutically acceptable salts thereof.

Compounds of formula I have affinity for dopamine D3 receptors and thus are useful in the treatment of conditions wherein modulation, especially antagonism/inhibition, of D3 receptors is beneficial, e.g. to treat drug dependency or as antipsychotic agents.

DETAILED DESCRIPTION OF THE INVENTION

Compounds of formula I and their pharmaceutically acceptable salts are useful in the treatment of all aspects of drug dependency, including drug intake, relapse to drug-seeking behaviour following abstinence and withdrawal symptoms from drugs of abuse such as alcohol, cocaine, opiates, nicotine, benzodiazepines and inhibition of tolerance induced by opioids, as well as for the treatment of drug craving. They also are useful as antipsychotic agents, for example in the treatment of schizophrenia, schizo-affective disorders, schizophreniform diseases, psychotic depression (which term includes bipolar depression, unipolar depression, single or recurrent major depressive episodes with or without psychotic features, catatonic features, melancholic features, atypical features or postpartum onset, seasonal affective disorder and dysthymia, depressive disorders resulting from a general medical condition including, but not limited to, myocardial infarction, diabetes, miscarriage or abortion), anxiety disorders (which includes generalized anxiety and social anxiety disorder), mania, acute mania, paranoid and delusional disorders. The compounds are also useful for the treatment of a family of related disorders referred to as somatoform disorders, as well as for the treatment of premature ejaculation. The compounds are further useful for the treatment of attention-deficit hyperactivity disorder (ADHD), addiction (smoking cessation, cocaine and others) and obsessive compulsive disorder (OCD).

Compounds of formula I can form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of formula I in this invention can be derivatized at functional groups to provide derivatives which are capable of conversion back to the parent compound in vivo. Physiologically acceptable and metabolically labile derivatives, which are capable of producing the parent compounds of formula I in vivo are also within the scope of this invention.

As used herein, the term "$C_{1-6}$-alkyl" is the same as "lower alkyl" and denotes monovalent linear or branched saturated hydrocarbon moiety, consisting solely of carbon and hydrogen atoms, having from 1 to 6 carbon atoms, for example, methyl, ethyl, propyl, isopropyl, n-butyl, iso-butyl, sec-butyl, tert-butyl and the like. Preferred alkyl groups are groups with 1, 2, 3 or 4 carbon atoms. Most preferred alkyl groups are methyl and ethyl.

The phrase "$C_{1-6}$-alkyl substituted by" refers to lower alkyl, which is substituted by one or multiple substituents, preferably 1-5 substituents, selected from the group as specified for the specific "$C_{1-6}$-alkyl substituted by", i.e. for example halogen or cycloalkyl. Preferred substituents are fluoro and cyclopropyl. Preferred substituted $C_{1-6}$-alkyl are cyclopropyl-$C_{1-6}$-alkyl, cycloalkyl-$C_{1-6}$-alkyl, fluoro-$C_{1-6}$-alkyl and halogen-$C_{1-6}$-alkyl. Most preferred are cyclopropyl-ethyl and fluoro-methyl.

The term "halogen" denotes chlorine (Cl), iodine (I), fluorine (F) and bromine (Br). Preferred halogen is fluorine.

The term "$C_{1-6}$-alkoxy" denotes a group —O—R' wherein R' is $C_{1-6}$-alkyl as defined above.

The phrase "3 to 6 membered monocyclic cycloalkyl" refers to a monovalent saturated monocyclic hydrocarbon radical of 3 to 6 ring carbon atoms. Examples are cyclopropyl, cyclobutenyl, cyclopentyl or cyclohexyl. Preferred examples are cyclopropyl, cyclopentyl and cyclohexyl. Preferred is cyclopropyl.

The term "aryl" refers to an aromatic carbocyclic group comprising 6 to 14, preferably 6 to 10, carbon atoms and having at least one aromatic ring or multiple condensed rings in which at least one ring is aromatic, for example phenyl (Ph), benzyl, naphthyl, biphenyl or indanyl. Preferred aryl group is phenyl. Aryl can be substituted by 1 to 3 halogen atoms. Preferred substituted aryl groups are halogen-phenyl, fluoro-phenyl, and fluoro-aryl. Most preferred is 4-fluoro-phenyl.

The term "heteroaryl", alone or in combination with other groups, refers to an aromatic cyclic group of having a single 4 to 8 membered ring or multiple condensed rings comprising 6 to 14, more preferably 6 to 10, ring atoms and containing 1, 2 or 3 heteroatoms selected from N, O and S, in which group at least one heterocyclic ring is aromatic. Examples of such groups include pyrrolyl, thienyl, furyl, pyrazolyl (pyrazyl), imidazolyl, triazolyl, tetrazolyl, thiazolyl, isothiazolyl, oxazolyl, isoxazolyl, pyridinyl, pyrimidinyl, pyrazinyl, pyridazinyl, indolyl, indazolyl, quinolinyl, isoquinolinyl, benzofuryl, benzothiazolyl, benzotriazolyl, benzoimidazolyl, benzooxazinyl, benzothiazinyl, benzothienyl and the like. A preferred heteroaryl group is pyridinyl. Heteroaryl can be substituted by 1 to 3 halogen atoms. Preferred substituents are H, F and Me. Preferred substituted heteroaryl groups are halogen-pyridinyl, fluoro-heteroaryl and fluoro-pyridinyl. Most preferred is 2-fluoro-pyridinyl.

"Pharmaceutically acceptable," such as pharmaceutically acceptable carrier, excipient, etc., means pharmacologically acceptable and substantially non-toxic to the subject to which the particular compound is administered.

The terms "pharmaceutically acceptable salt" and "pharmaceutically acceptable acid addition salt" embrace salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

In detail, the present invention provides compounds of formula I,

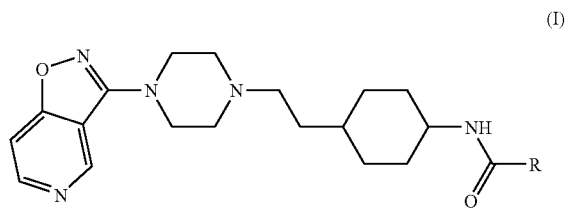

(I)

wherein:

R is $C_{1-6}$-alkyl;

$C_{1-6}$-alkyl substituted by one 3 to 6 membered monocyclic cycloalkyl, $C_{1-6}$-alkoxy, or 1 to 3 halogen atoms;

$C_{1-6}$-alkoxy;

aryl;

aryl substituted by 1 to 3 halogen atoms;

heteroaryl; or heteroaryl substituted by 1 to 3 halogen atoms;

as well as pharmaceutically acceptable salts thereof.

In a preferred embodiment, the present invention provides a compound of formula I, wherein R is $C_{1-6}$-alkyl optionally substituted by one 3 to 6 membered monocyclic cycloalkyl, $C_{1-6}$-alkoxy, or 1 to 3 halogen atoms;

$C_{1-6}$-alkoxy;

phenyl substituted by 1 to 3 halogen atoms; or pyridinyl substituted by 1 to 3 halogen atoms;

as well as pharmaceutically acceptable salts thereof.

In a preferred embodiment, the present invention provides a compound of formula I, wherein R is $C_{1-6}$-alkyl optionally substituted by one 3 to 6 membered monocyclic cycloalkyl;

$C_{1-6}$-alkoxy;

as well as pharmaceutically acceptable salts thereof.

In a preferred embodiment, the present invention provides a compound of formula I, wherein R is methyl, ethyl, cyclopropyl-ethyl, methoxy-ethyl, fluoro-methyl, fluorophenyl or fluoro-pyridinyl.

In a preferred embodiment the present invention relates e to a compound of formula (I'),

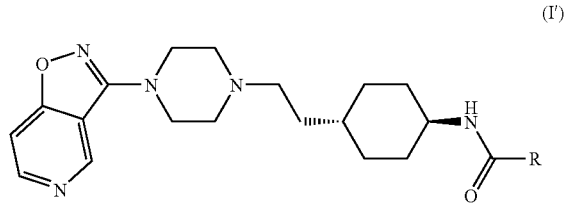

(I')

wherein R is defined as given above.

Special preference is given to a compound of formula (I') selected from the group consisting of:

N-{trans-4-[2-(4-Isoxazolo[4,5-c]pyridin-3-yl-piperazin-1-yl)-ethyl]-cyclohexyl}-acetamide;

N-{trans-4-[2-(4-Isoxazolo[4,5-c]pyridin-3-yl-piperazin-1-yl)-ethyl]-cyclohexyl}-3-methoxy-propionamide;
N-{trans-4-[2-(4-Isoxazolo[4,5-c]pyridin-3-yl-piperazin-1-yl)-ethyl]-cyclohexyl}-propionamide;
2-Cyclopropyl-N-{trans-4-[2-(4-isoxazolo[4,5-c]pyridin-3-yl-piperazin-1-yl)-ethyl]-cyclohexyl}-acetamide;
2-Fluoro-N-{trans-4-[2-(4-isoxazolo[4,5-c]pyridin-3-yl-piperazin-1-yl)-ethyl]-cyclohexyl}-acetamide;
4-Fluoro-N-{trans-4-[2-(4-isoxazolo[4,5-c]pyridin-3-yl-piperazin-1-yl)-ethyl]-cyclohexyl}-benzamide; and
6-Fluoro-N-{trans-4-[2-(4-isoxazolo[4,5-c]pyridin-3-yl-piperazin-1-yl)-ethyl]-cyclohexyl}-nicotinamide.

Special preference is given to a compound of formula (I') selected from the group consisting of:
N-{trans-4-[2-(4-Isoxazolo[4,5-c]pyridin-3-yl-piperazin-1-yl)-ethyl]-cyclohexyl}-acetamide;
N-{trans-4-[2-(4-Isoxazolo[4,5-c]pyridin-3-yl-piperazin-1-yl)-ethyl]-cyclohexyl}-3-methoxy-propionamide;
N-{trans-4-[2-(4-Isoxazolo[4,5-c]pyridin-3-yl-piperazin-1-yl)-ethyl]-cyclohexyl}-propionamide;
2-Cyclopropyl-N-{trans-4-[2-(4-isoxazolo[4,5-c]pyridin-3-yl-piperazin-1-yl)-ethyl]-cyclohexyl}-acetamide;

In one embodiment, the invention provides compounds of formula I wherein R is $C_{1-6}$-alkyl optionally substituted by one 3 to 6 membered monocyclic cycloalkyl; or $C_{1-6}$-alkoxy; as well as pharmaceutically acceptable salts thereof.

In one embodiment, the invention provides compounds of formula I wherein R is $C_{1-6}$-alkyl.

In one embodiment, the invention provides compounds of formula I wherein R is methyl.

In one embodiment, the invention provides compounds of formula I wherein R is $C_{1-6}$-alkyl substituted by one 3 to 6 membered monocyclic cycloalkyl, $C_{1-6}$alkoxy, or 1 to 3 halogen atoms.

In one embodiment, the invention provides compounds of formula I wherein R is fluoro-methyl.

In one embodiment, the invention provides compounds of formula I wherein R is cyclopropyl-ethyl.

In one embodiment, the invention provides compounds of formula I wherein R is $C_{1-6}$-alkoxy.

In one embodiment, the invention provides compounds of formula I wherein R is ethoxy-ethyl.

In one embodiment, the invention provides compounds of formula I wherein R is aryl substituted by 1 to 3 halogen atoms.

In one embodiment, the invention provides compounds of formula I wherein R is fluoro-phenyl.

In one embodiment, the invention provides compounds of formula I wherein R is heteroaryl substituted by 1 to 3 halogen atoms.

In one embodiment, the invention provides compounds of formula I wherein R is fluoro-pyridinyl.

In a further aspect of the present invention, provide pharmaceutical compositions containing a therapeutically effective amount of a compound of formula (I) or a pharmaceutically acceptable salt thereof and a pharmaceutically acceptable carrier.

A further aspect of the present invention provides a method for the treatment of schizophrenia, cognitive disorders and drug addiction by administering a compound of formula (I) or (I') or a pharmaceutically acceptable salt thereof.

A further aspect of the present invention provides a method for the treatment or prevention of diseases related to the D3 receptor by administering a compound of formula I or a pharmaceutically acceptable salt thereof.

A further aspect of the present invention provides a method for the therapeutic and/or prophylactic treatment of a disorder or condition mediated by the D3 receptor binding site, or that can be treated via modulation of the D3 receptor binding site, particularly for the therapeutic and/or prophylactic treatment of cognitive disorders, drug addiction, depression, anxiety, drug dependence, dementias, memory impairment, psychotic disorders comprising schizophrenia, schizoaffective disorders, bipolar disease, mania, psychotic depression, psychoses comprising paranoia and delusions, attention-deficit hyperactivity disorder, addiction and obsessive compulsive disorder, which method comprises administering a compound according to any of claims 1-5 to a human being or animal.

A further aspect of the present invention provides the process for the manufacture of compounds of formula I as defined above.

The preparation of compounds of formula I of the present invention can be carried out in sequential or convergent synthetic routes. Syntheses of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the description or in the examples, or by methods known in the art.

A preferred embodiment of the process for preparing a compound of formula I,

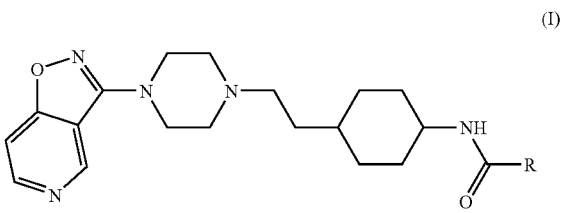

(I)

wherein R has the meaning as given above, comprises one of the following steps:

a) reductive amination of an aldehyde of formula (I-1) with a 3-piperazine-1-yl-isoxazolo[4,5-c]pyridine of formula (I-2) in the presence of a reducing agent, and (I-1)

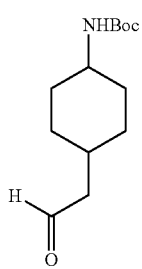

(I-2)

removing the Boc protecting group under acidic conditions to yield amine intermediate of formula (I-3)

(I-3)

and b) coupling of amine intermediate of formula (I-3) with a carboxylic acid R—COOH or acid chloride R—COCl to yield compound of formula I.

The ability of the compounds to bind to the $D_3$ receptors was determined using radioligand binding to cloned receptors selectively expressed in HEK-293 EBNA cells.

Biological Data

Membrane Preparation for Human $D_3$ Receptors

HEK-293 EBNA cells were transiently transfected with expression plasmids encoding for the human $D_3$ dopamine receptor. The cells were harvested 48 h post-transfection, washed three times with cold PBS and stored at −80° C. prior to use. The pellet was suspended in cold 50 mM Tris-HCl buffer containing 10 mM EDTA (pH 7.4) and homogenized with a Polytron (Kinematica AG, Basel, Switzerland) for 20-30 sec at 12.000 rpm. After centrifugation at 48.000×g for 30 min at 4° C., the pellet was resuspended in cold 10 mM Tris-HCl buffer containing 0.1 mM EDTA (pH 7.4), homogenized, and centrifuged as above. This pellet was further resuspended in a smaller volume of ice cold 10 mM Tris-HCl buffer containing 0.1 mM EDTA (pH 7.4) and homogenized with a Polytron for 20-30 sec at 12.000 rpm. The protein content of this homogenate was determined with the Bio-Rad (Bradford) Protein Assay (Biorad Laboratories GmbH, München, Germany) according to the instructions of the manufacturer using gamma globulin as the standard. This homogenate was stored at −80° C. in aliquots and thawed immediately prior to use.

Radioligand Binding Assay Conditions

Aliquots of membrane preparations were thawed at RT, resuspended in assay buffer (50 mM Tris-HCl, 120 mM NaCl, 5 mM $MgCl_2$, 1 mM EDTA, 5 mM KCl, 1.5 mM $CaCl_2$, pH=7.4), homogenized with a Polytron for 20-30 sec at 12.000 rpm and adjusted to a final concentration of approximately 7.5 µg protein/well.

The binding affinity (Ki) of the compounds was determined using radioligand binding. Membranes were incubated in a total volume of 200 µl with a fixed concentration of radioligand (final concentration approximately 0.5 nM [$^3$H]-spiperone) and ten concentrations of test compound in ranging between 10 µM-0.1 nM for 1 h at RT. At the end of the incubation, the reaction mixtures were filtered on to unifilter 96-well white microplates with bonded GF/C filters (Packard BioScience, Zürich, Switzerland; preincubated for 1 h in 0.1% polyethylenimine (PEI) in assay buffer) with a Filtermate 196 harvester (Packard BioScience) and washed 3 times with cold assay buffer. The nonspecific binding was determined with equally composed reaction mixtures in the presence of 10 µM unlabelled spiperone. Per well 45 µl of Microscint 40 (Perkin Elmer, Schwerzenbach, Switzerland) was added, plates for sealed, shaken for 20 min and counted for 3 min on a Topcount Microplate Scintillation Counter (Canberra Packard SA, Zürich, Switzerland) with quenching correction.

Data Calculation

The CPM value for each duplicate of a concentration of competing compound was averaged (y1), then the % specific binding was calculated according to the equation (((y1−non-specific)/(total binding−non-specific))×100). Graphs were plotted with the % specific binding using XLfit, a curve fitting program that iteratively plots the data using Levenburg Marquardt algorithm. The single site competition analysis equation used was $y=A+((B-A)/(1+((x/C)^D)))$, where y is the % specific binding, A is the minimum y, B is the maximum y, C is the $IC_{50}$, x is the $\log_{10}$ of the concentration of the competing compound and D is the slope of the curve (the Hill Coefficient). From these curves the $IC_{50}$ (inhibition concentration at which 50% specific binding of the radioligand was displaced) and Hill coefficient were determined. The affinity constant (Ki) was calculated using the Cheng-Prusoff equation Ki=$(IC_{50}/1+([L]/Kd)$, where [L] is the concentration of radioligand and Kd is the dissociation constant of the radioligand at the receptor as determined by the saturation isotherm.

The compounds of the present invention are potent modulators of the dopamine $D_3$ receptors as shown in the activity table hereinafter which gives the Ki values in µM for the dopamine $D_3$ receptors for some examples of the compounds of the present invention:

TABLE 1 acticity table: human Ki values of selected examples

| Ex. | Compound | Name | Ki dopamine D3 receptor: Human D3 |
|---|---|---|---|
| 1 | | N-{trans-4-[2-(4-Isoxazolo[4,5-c]pyridin-3-yl-piperazin-1-yl)-ethyl]-cyclohexyl}-acetamide | 0.040398 |
| 2 | | N-{trans-4-[2-(4-Isoxazolo[4,5-c]pyridin-3-yl-piperazin-1-yl)-ethyl]-cyclohexyl}-3-methoxy-propionamide | 0.024261 |
| 3 | | N-{trans-4-[2-(4-Isoxazolo[4,5-c]pyridin-3-yl-piperazin-1-yl)-ethyl]-cyclohexyl}-propionamide | 0.012364 |
| 4 | | 2-Cyclopropyl-N-{trans-4-[2-(4-isoxazolo[4,5-c]pyridin-3-yl-piperazin-1-yl)-ethyl]-cyclohexyl}-acetamide | 0.015422 |
| 5 | | 2-Fluoro-N-{trans-4-[2-(4-isoxazolo[4,5-c]pyridin-3-yl-piperazin-1-yl)-ethyl]-cyclohexyl}-acetamide | 0.043 |
| 6 | | 4-Fluoro-N-{trans-4-[2-(4-isoxazolo[4,5-c]pyridin-3-yl-piperazin-1-yl)-ethyl]-cyclohexyl}-benzamide | 0.097 |

TABLE 1-continued activity table: human Ki values of selected examples

| Ex. | Compound | Name | Ki dopamine D3 receptor: Human D3 |
|---|---|---|---|
| 7 | | 6-Fluoro-N-{trans-4-[2-(4-isoxazolo[4,5-c]pyridin-3-yl-piperazin-1-yl)-ethyl]-cyclohexyl}-nicotinamide | 0.063 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such as carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Synthesis

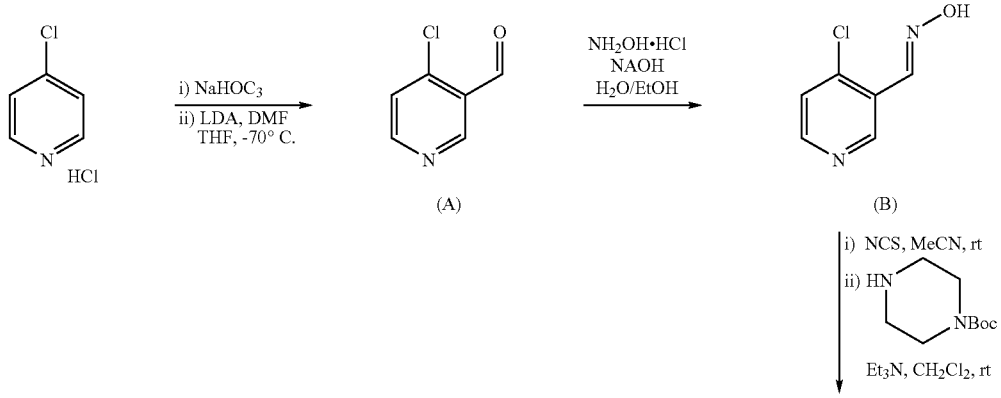

Scheme 1: General synthesis route

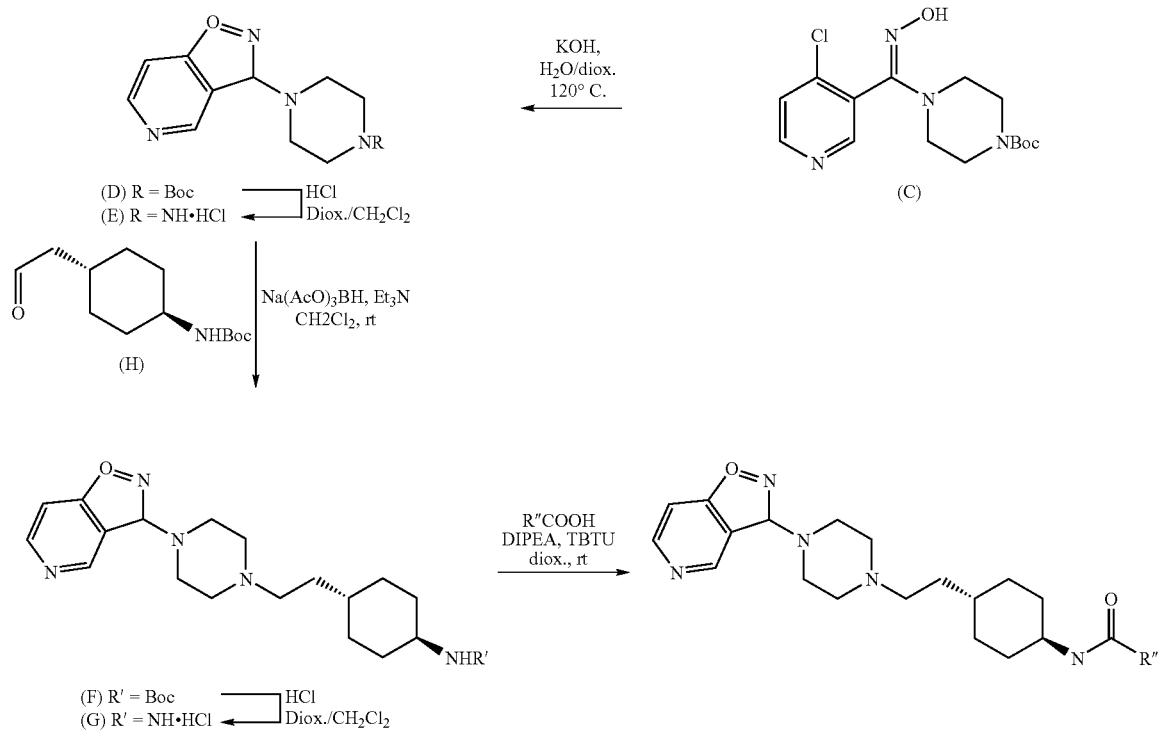

Synthesis of aldehyde (A) is described in *Biorg. Med. Chem. Lett* 17 (2007), 662-667. (A) is transformed into the corresponding oxime (B), followed by the reaction with tert-butyl 1-piperazinecarboxylate leading to intermediate (C). Ring closure is performed with KOH whereupon intermediate (D) is obtained. After the removal of protecting group Boc, (E) is reacted with trans-[4-(2-oxo-ethyl)-cyclohexyl]-carbamic acid tert-butyl ester leading to intermediate (G) via (F). The final product is obtained by reacting the free amino function with the desired carboxylic acid.

Experimental Part

The following examples are provided to further elucidate the invention.

Example 1

N-{trans-4-[2-(4-Isoxazolo[4,5-c]pyridin-3-yl-piperazin-1-yl)-ethyl]-cyclohexyl}-acetamide

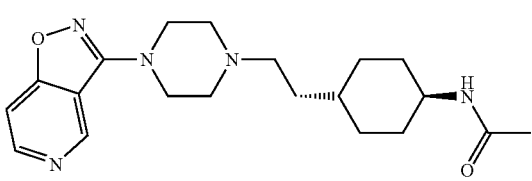

Step 1: 4-Chloro-pyridine-3-carbaldehyde (Intermediate A)

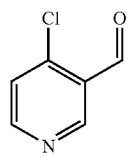

The title compound can be prepared starting from 4-chloropyridine hydrochloride by published methods (*Bioorg. Med. Chem. Lett.* 17 (2007), 662-667).

Step 2: 4-Chloro-pyridine-3-carbaldehyde Oxime (Intermediate B)

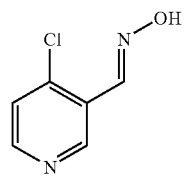

4-Chloro-pyridine-3-carbaldehyde (10.0 g, 71 mmol) was dissolved in EtOH (12 ml). $H_2O$ (30 ml), ice (30 g) and hydroxylamine hydrochloride (5.40 g, 78 mmol) were added. To the resulting mixture was added over a period of 2 min a solution of 2 N NaOH (88.3 ml, 177 mmol). The resulting yellowish solution was stirred 2.5 h at r.t. before neutralisation with AcOH (pH=6). White crystals precipitated, were collected by filtration and washed with H₂O (30 ml). The product was dried 1 h at 50° C. on the high vacuum to yield 9.25 g (84%) of a off white solid. m/z=157.1 ([M–H]⁻).

Step 3: 4-{(4-Chloro-pyridin-3-yl)-[(E,Z)-hydroxyimino]-methyl}-piperazine-1-carboxylic acid tert-butyl ester (Intermediate C)

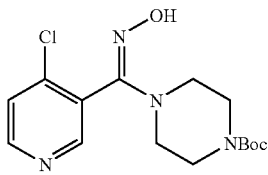

4-Chloro-pyridine-3-carbaldehyde oxime (4.00 g, 26 mmol) was dissolved in MeCN (40 ml) and N-chlorosuccinimide (3.58 g, 27 mmol) was added in portions (slightly exothermic reaction). The yellowish solution was stirred 30 min more before addition of H₂O and extraction with two portions of EtOAc. The organic layers were washed with more H₂O and brine and dried over Na₂SO₄. The solvent was evaporated to dryness and the residue was dissolved in CH₂Cl₂ (80 ml). Et₃N (3.72 ml, 27 mmol) was added to obtain a red solution. tert-Butyl 1-piperazinecarboxylate (5.23 g, 28 mmol) was added in portions and the resulting reaction mixture was stirred 30 min at r.t. Sat. aq. Na₂CO₃ was added and the product was extracted with CH₂Cl₂. After drying (Na₂SO₄) and evaporation of the solvent the product was purified by flash chromatography (100 g SiO₂, Hept/EtOAc 70:30→0:100) yielding 2.37 g (27%) of the title compound as a yellow gum. m/z=341.1 ([M+H]⁺).

Step 4: 4-Isoxazolo[4,5-c]pyridin-3-yl-piperazine-1-carboxylic acid tert-butyl ester (Intermediate D)

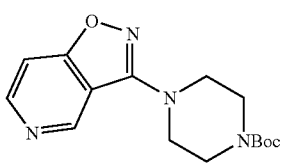

4-{(4-Chloro-pyridin-3-yl)-[(E,Z)-hydroxyimino]-methyl}-piperazine-1-carboxylic acid tert-butyl ester (2.36 g, 6.9 mmol) was dissolved in dioxane (20 ml) and 30% aq. KOH (40 ml) was added. After stirring 16 h at 120° C. (reflux) a clear two phases mixture was obtained. After cooling the organic layer was collected and the aqueous phase was extracted with CH₂Cl₂. The combined organic layers were dried (Na₂SO₄) and the solvent was evaporated. Flash chromatography (50 g SiO₂, Hept/EtOAc 30:70→0:100) yielded 960 mg (45%) of the title compound as an off white solid. m/z=305.3 ([M+H]⁺).

Step 5: 3-piperazin-1-yl-isoxazolo[4,5-c]pyridine dihydrochloride (Intermediate E)

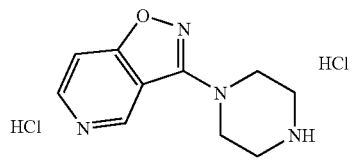

4-Isoxazolo[4,5-c]pyridin-3-yl-piperazine-1-carboxylic acid tert-butyl ester (960 mg, 3.1 mmol) was dissolved in CH₂Cl₂ (2 ml) and 4 N HCl in dioxane (15.7 ml, 63 mmol) was added. The resulting mixture was stirred 16 h at r.t. After dilution with ⁱPr₂O the product was collected by filtration and washed with one portion of ⁱPr₂O before drying it under high vacuum at 50° C. to obtain 850 mg (97%) as a pink solid. m/z=205.2 ([M+H]⁺).

Step 6: {Trans-4-[2-(4-Isoxazolo[4,5-c]pyridin-3-yl-piperazin-1-yl)-ethyl]-cyclohexyl}-carbamic acid tert-butyl ester (Intermediate F)

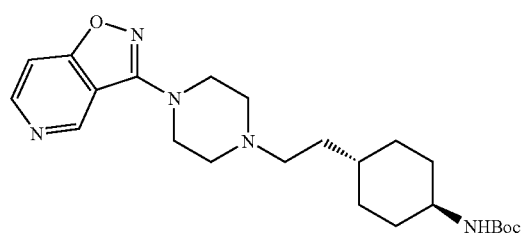

A solution in CH₂Cl₂ (10 ml) of 3-piperazin-1-yl-isoxazolo[4,5-c]pyridine dihydrochloride (840 mg, 3.0 mmol) and trans-[4-(2-oxo-ethyl)-cyclohexyl]-carbamic acid tert-butyl ester (904 mg, 3.7 mmol; intermediate H; prepared according to WO2007/093540) was treated with Et₃N (629 mg, 6.2 mmol) before addition of Na(AcO)₃BH (1.03 g, 5 mmol). The reaction mixture was stirred 16 h at r.t., then sat. aq. NaHCO₃ was added and the product was extracted with 2 portions of CH₂Cl₂. After drying (MgSO₄) and evaporation of the solvent the product was purified by flash chromatography (50 g SiO₂, EtOAc/MeOH 100:0→80:20) to obtain 930 mg (71%) of the title compound as an off white solid. m/z=430.3 ([M+H]⁺).

Step 7: trans-4-[2-(4-Isoxazolo[4,5-c]pyridin-3-yl-piperazin-1-yl)-ethyl]-cyclohexylamine dihydrochloride (Intermediate G)

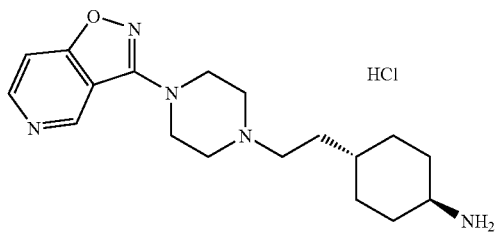

{trans-4-[2-(4-Isoxazolo[4,5-c]pyridin-3-yl-piperazin-1-yl)-ethyl]-cyclohexyl}-carbamic acid tert-butyl ester (930 mg, 2.2 mmol) was dissolved in $CH_2Cl_2$ (3 ml) and 4 N HCl in dioxane (10.8 ml, 43 mmol) was added. The resulting mixture was stirred 16 h at r.t. After dilution with $^iPr_2O$ the product was collected by filtration and washed with one portion of $^iPr_2O$ before drying it under high vacuum at 50° C. to obtain 686 mg (79%) as a white solid. m/z=330.3 ([M+H]$^+$).

Step 8: N-{trans-4-[2-(4-Isoxazolo[4,5-c]pyridin-3-yl-piperazin-1-yl)-ethyl]-cyclohexyl}-acetamide A mixture in dioxane (5 ml) of trans-4-[2-(4-isoxazolo[4,5-c]pyridin-3-yl-piperazin-1-yl)-ethyl]-cyclohexylamine dihydrochloride (100 mg, 0.25 mmol), AcOH (22 mg, 0.37 mmol), $^iPr_2NEt$ (161 mg, 1.2 mmol) and TBTU (96 mg, 0.30 mmol) was stirred 16 h at r.t. After evaporation to dryness sat. aq. $NaHCO_3$ was added and the product was extracted with 2 portions of $CH_2Cl_2$. The organic layers were directly loaded on a column. Flash chromatography (20 g $SiO_2$, $CH_2Cl_2$/MeOH 100:0→90:10) yielded 62 mg (67%) of the title compound as white solid. m/z=372.2 ([M+H]$^+$).

Examples 2-7

Examples 2-7 were prepared in analogy to example 1 starting from trans-4-[2-(4-isoxazolo[4,5-c]pyridin-3-yl-piperazin-1-yl)-ethyl]-cyclohexylamine dihydrochloride (Intermediate G) and an appropriate carboxylic acid.

TABLE 2 examples 2-7

| Ex. | Compound | Carboxylic acid | m/z ([M + H]$^+$) |
|---|---|---|---|
| 2 | N-{trans-4-[2-(4-Isoxazolo[4,5-c]pyridin-3-yl-piperazin-1-yl)-ethyl]-cyclohexyl}-3-methoxy-propionamide | from 3-methoxypropionic acid | 416.3 |
| 3 | N-{trans-4-[2-(4-Isoxazolo[4,5-c]pyridin-3-yl-piperazin-1-yl)-ethyl]-cyclohexyl}-propionamide | from propionic acid | 386.3 |
| 4 | 2-Cyclopropyl-N-{trans-4-[2-(4-isoxazolo[4,5-c]pyridin-3-yl-piperazin-1-yl)-ethyl]-cyclohexyl}-acetamide | from cyclopropyl-acetic acid | 412.4 |
| 5 | 2-Fluoro-N-{trans-4-[2-(4-isoxazolo[4,5-c]pyridin-3-yl-piperazin-1-yl)-ethyl]-cyclohexyl}-acetamide | from sodium fluoroacetate | 390.4 |
| 6 | 4-Fluoro-N-{trans-4-[2-(4-isoxazolo[4,5-c]pyridin-3-yl-piperazin-1-yl)-ethyl]-cyclohexyl}-benzamide | from 4-fluorobenzoic acid | 452.3 |
| 7 | 6-Fluoro-N-{trans-4-[2-(4-isoxazolo[4,5 c]pyridin-3-yl-piperazin-1-yl)-ethyl]-cyclohexyl}-nicotinamide | from 6-fluoronicotinic acid | 453.3 |

Pharmaceutical Preparations

Example A

Film coated tablets containing the following ingredients can be manufactured in a conventional manner:

TABLE 3

| Example of film coated tablets | | |
|---|---|---|
| Ingredients | Per tablet | |
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

TABLE 4

Example of capsules

| Ingredients | Per capsule |
| --- | --- |
| Compound of formula I | 25.0 mg |
| Lactose | 150.0 mg |
| Maize starch | 20.0 mg |
| Talc | 5.0 mg |

The components are sieved and mixed and filled into capsules of size 2 or another suitable size.

Example C

Injection solutions can have the following composition:

TABLE 5

Example of injection solutions

| | |
| --- | --- |
| Compound of formula I | 3.0 mg |
| Gelatin | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

TABLE 6

Example of soft gelatin capsules

| Capsule contents | |
| --- | --- |
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Capsule contents | |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

TABLE 7

Example of sachets

| | |
| --- | --- |
| Compound of formula I | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

The invention claimed is:

1. A compound of formula I:

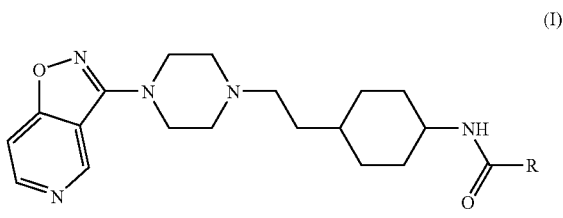

wherein:

R is $C_{1-6}$-alkyl;

$C_{1-6}$-alkyl substituted by one 3 to 6 membered monocyclic cycloalkyl, $C_{1-6}$-alkoxy, or 1 to 3 halogen atoms;

$C_{1-6}$-alkoxy;

aryl;

aryl substituted by 1 to 3 halogen atoms;

heteroaryl; or heteroaryl substituted by 1 to 3 halogen atoms, or a pharmaceutically acceptable salt thereof.

2. The compound of claim 1, wherein:

R is $C_{1-6}$-alkyl optionally substituted by one 3 to 6 membered monocyclic cycloalkyl, $C_{1-6}$alkoxy, or 1 to 3 halogen atoms;

$C_{1-6}$-alkoxy;

phenyl substituted by 1 to 3 halogen atoms; or pyridinyl substituted by 1 to 3 halogen atoms;

or a pharmaceutically acceptable salt thereof.

3. The compound of claim 2, wherein R is methyl, ethyl, cyclopropyl-ethyl, methoxy-ethyl, fluoro-methyl, fluorophenyl or fluoro-pyridinyl.

4. The compound of claim 2, wherein:

R is $C_{1-6}$-alkyl optionally substituted by one 3 to 6 membered monocyclic cycloalkyl $C_{1-6}$-alkoxy;

or a pharmaceutically acceptable salt thereof.

5. The compound of claim 1 having formula (I'):

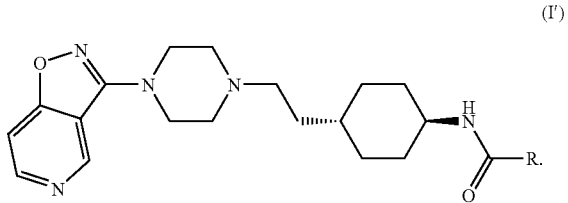

(I')

6. The compound of claim 5 selected from the group consisting of:
N-{trans-4-[2-(4-Isoxazolo[4,5-c]pyridin-3-yl-piperazin-1-yl)-ethyl]-cyclohexyl}-acetamide;
N-{trans-4-[2-(4-Isoxazolo[4,5-c]pyridin-3-yl-piperazin-1-yl)-ethyl]-cyclohexyl}-3-methoxy-propionamide;
N-{trans-4-[2-(4-Isoxazolo[4,5-c]pyridin-3-yl-piperazin-1-yl)-ethyl]-cyclohexyl}-propionamide;
2-Cyclopropyl-N-{trans-4-[2-(4-isoxazolo[4,5-c]pyridin-3-yl-piperazin-1-yl)-ethyl]-cyclohexyl}-acetamide;
2-Fluoro-N-{trans-4-[2-(4-isoxazolo[4,5-c]pyridin-3-yl-piperazin-1-yl)-ethyl]-cyclohexyl}-acetamide;
4-Fluoro-N-{trans-4-[2-(4-isoxazolo[4,5-c]pyridin-3-yl-piperazin-1-yl)-ethyl]-cyclohexyl}-benzamide; and
6-Fluoro-N-{trans-4-[2-(4-isoxazolo[4,5-c]pyridin-3-yl-piperazin-1-yl)-ethyl]-cyclohexyl}-nicotinamide.

7. The compound of claim 6 selected from the group consisting of:
N-{trans-4-[2-(4-Isoxazolo[4,5-c]pyridin-3-yl-piperazin-1-yl)-ethyl]-cyclohexyl}-acetamide;
N-{trans-4-[2-(4-Isoxazolo[4,5-c]pyridin-3-yl-piperazin-1-yl)-ethyl]-cyclohexyl}-3-methoxy-propionamide;
N-{trans-4-[2-(4-Isoxazolo[4,5-c]pyridin-3-yl-piperazin-1-yl)-ethyl]-cyclohexyl}-propionamide; and
2-Cyclopropyl-N-{trans-4-[2-(4-isoxazolo[4,5-c]pyridin-3-yl-piperazin-1-yl)-ethyl]-cyclohexyl}-acetamide.

8. The compound of claim 1, wherein R is $C_{1-6}$alkyl.

9. The compound of claim 8, wherein R is methyl.

10. The compound of claim 1, wherein R is $C_{1-6}$-alkyl optionally substituted by one 3 to 6 membered monocyclic cycloalkyl, $C_{1-6}$alkoxy, or 1 to 3 halogen atoms.

11. The compound of claim 10, wherein R is fluoro-methyl.

12. The method of claim 10, wherein R is cyclopropyl-ethyl.

13. The compound of claim 10, wherein R is ethoxy-ethyl.

14. The compound of claim 1, wherein R is $C_{1-6}$alkoxy.

15. The compound of claim 1, wherein R is aryl.

16. The compound of claim 1, wherein R is aryl substituted by 1 to 3 halogen atoms.

17. The compound of claim 16, wherein R is fluoro-phenyl.

18. The compound of claim 1, wherein R is heteroaryl.

19. The compound of claim 1, wherein R is heteroaryl substituted by 1 to 3 halogen atoms.

20. The compound of claim 19, wherein R is fluoro-pyridinyl.

21. A pharmaceutical composition comprising a therapeutically effective amount of a compound of formula I

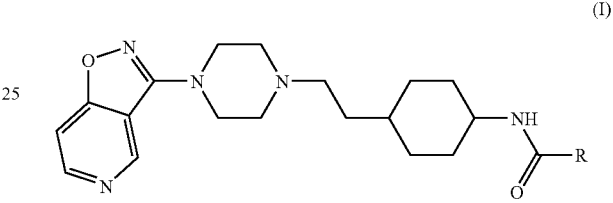

(I)

wherein:
R is $C_{1-6}$-alkyl;
$C_{1-6}$-alkyl substituted by one 3 to 6 membered monocyclic cycloalkyl, $C_{1-6}$alkoxy, or 1 to 3 halogen atoms;
$C_{1-6}$-alkoxy;
aryl;
aryl substituted by 1 to 3 halogen atoms;
heteroaryl; or
heteroaryl substituted by 1 to 3 halogen atoms,
or a pharmaceutically acceptable salt thereof and a pharmaceutically acceptable carrier.

* * * * *